(12) United States Patent
Kozak

(10) Patent No.: US 9,815,187 B2
(45) Date of Patent: Nov. 14, 2017

(54) TOOL ACCESSORY HAVING A PARTIALLY REMOVABLE ATTACHMENT PORTION

(71) Applicant: Burton Kozak, Chicago, IL (US)

(72) Inventor: Burton Kozak, Chicago, IL (US)

( * ) Notice: Subject to any disclaimer, the term of this patent is extended or adjusted under 35 U.S.C. 154(b) by 139 days.

(21) Appl. No.: 14/221,914

(22) Filed: Mar. 21, 2014

(65) Prior Publication Data

US 2015/0266102 A1 Sep. 24, 2015

(51) Int. Cl.
| | |
|---|---|
| B27B 19/00 | (2006.01) |
| B25F 3/00 | (2006.01) |
| B23D 61/00 | (2006.01) |
| B25F 1/00 | (2006.01) |
| B25F 1/02 | (2006.01) |
| A61B 17/14 | (2006.01) |

(52) U.S. Cl.
CPC .............. *B25F 3/00* (2013.01); *A61B 17/142* (2016.11); *B23D 61/006* (2013.01); *B25F 1/006* (2013.01); *B25F 1/02* (2013.01); *Y10T 279/3406* (2015.01)

(58) Field of Classification Search
CPC .... B25F 3/00; Y10T 279/3406; B27B 19/006; A61B 17/14; A61B 17/141; A61B 17/148; A61B 17/174; A61B 17/142; B23D 61/006; B23D 51/10; B24B 23/04; B28D 1/127
USPC .............. 279/143; 83/698.41; 451/359, 357; 411/539
See application file for complete search history.

(56) References Cited

U.S. PATENT DOCUMENTS

| | | | | |
|---|---|---|---|---|
| 760,914 | A * | 5/1904 | Newberry | F16B 43/007 301/68 |
| 2,658,699 | A * | 11/1953 | Rovas | D04B 27/00 242/118.5 |
| 3,017,908 | A * | 1/1962 | Higbee | B23D 51/10 30/166.3 |
| 3,491,647 | A * | 1/1970 | Frazier | F16B 43/007 411/532 |
| 5,106,252 | A * | 4/1992 | Shapton | F16B 43/007 411/519 |
| 5,366,312 | A * | 11/1994 | Raines | B24B 45/00 30/340 |
| 5,735,866 | A * | 4/1998 | Adams | A61B 17/14 30/339 |

(Continued)

FOREIGN PATENT DOCUMENTS

| | | |
|---|---|---|
| AU | 2013205490 A1 | 5/2013 |
| DE | 102007036322 A1 * 10/2008 | ............. A61F 15/02 |

(Continued)

OTHER PUBLICATIONS

International Search Report and Written Opinion for corresponding PCT application No. PCT/US2015/021659 dated Jul. 8, 2015, 10 pages.

*Primary Examiner* — Sunil K Singh
*Assistant Examiner* — Paul M Janeski
(74) *Attorney, Agent, or Firm* — Factor Intellectual Property Law Group

(57) ABSTRACT

A tool accessory having an attachment portion having a first aperture for attaching to a tool and a removable portion, wherein in a first configuration the removable portion is engaged with the attachment portion, and in a second configuration the removable portion is disengaged from the attachment portion.

20 Claims, 4 Drawing Sheets

(56) References Cited

U.S. PATENT DOCUMENTS

| | | | |
|---|---|---|---|
| 8,464,622 B2 * | 6/2013 | Chen | B23D 61/023 83/835 |
| D694,598 S * | 12/2013 | Davidian | D8/20 |
| 2014/0033880 A1 | 2/2014 | Hill | |
| 2014/0035242 A1 | 2/2014 | Kaye et al. | |

FOREIGN PATENT DOCUMENTS

| | | | | |
|---|---|---|---|---|
| DE | EP 2499978 A1 * | 9/2012 | | B23D 51/10 |
| WO | 2013077862 A1 | 5/2013 | | |

* cited by examiner

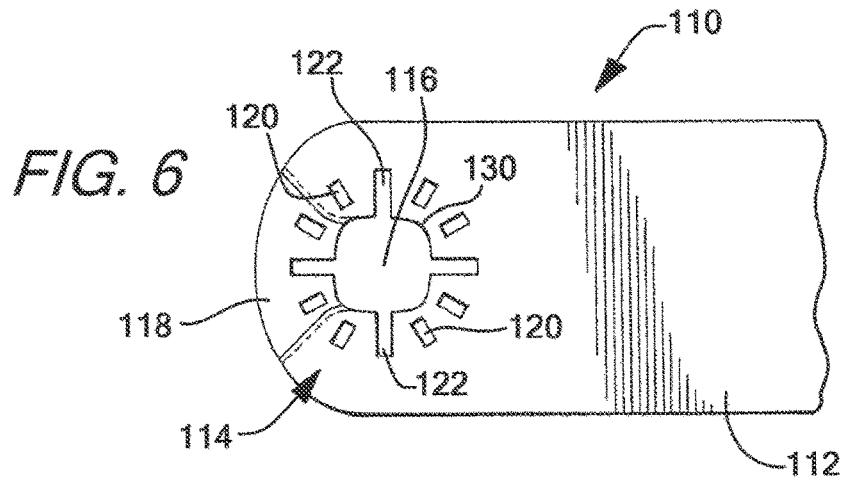
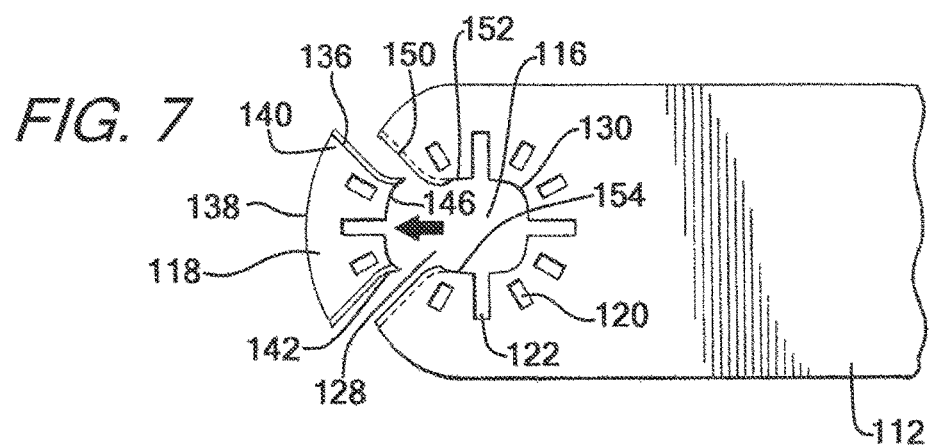
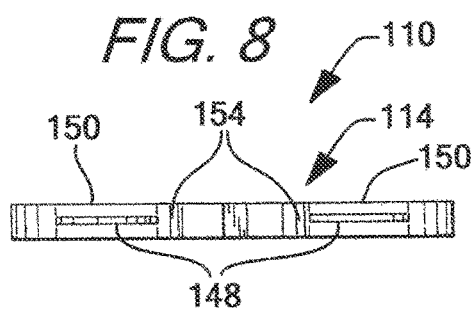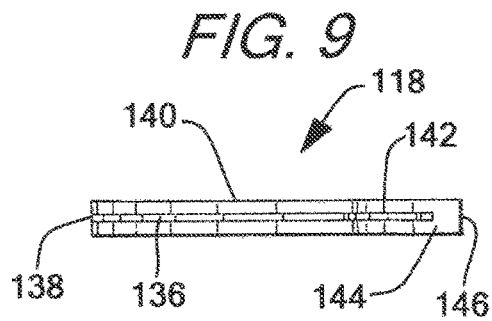

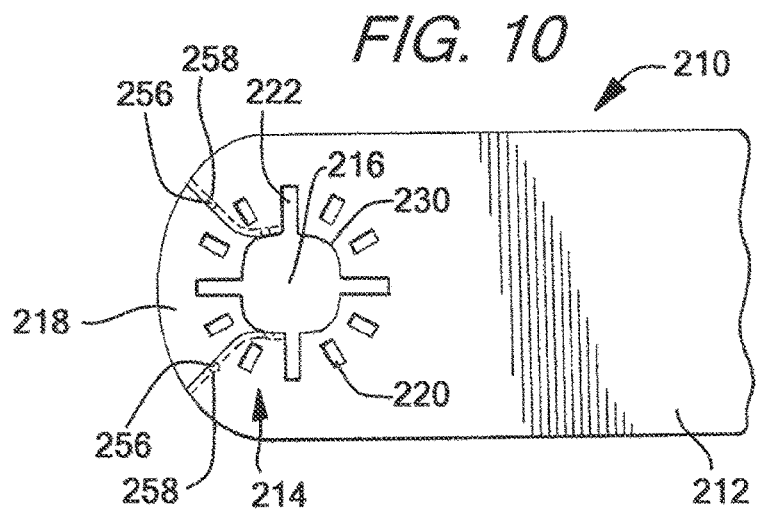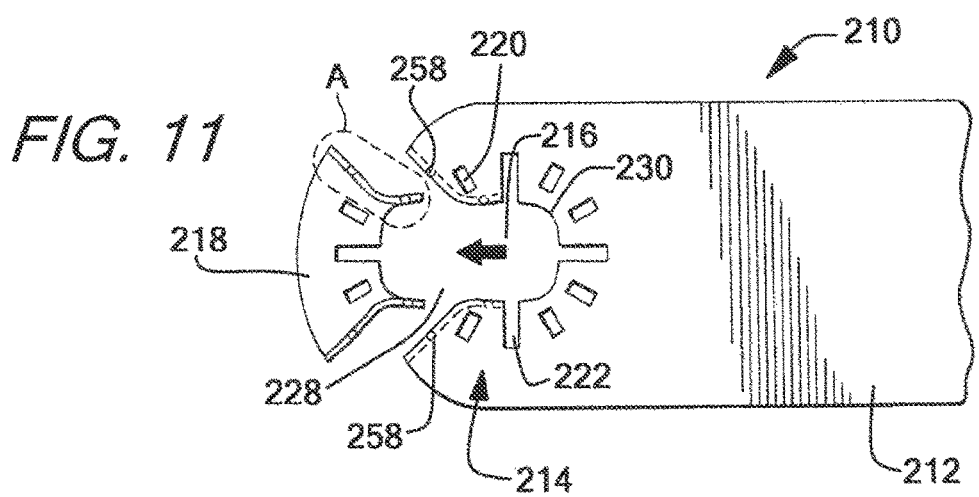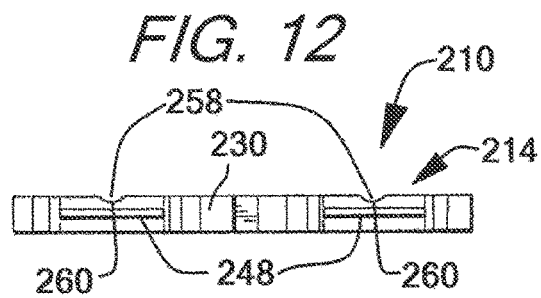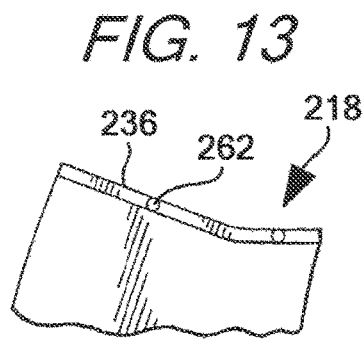

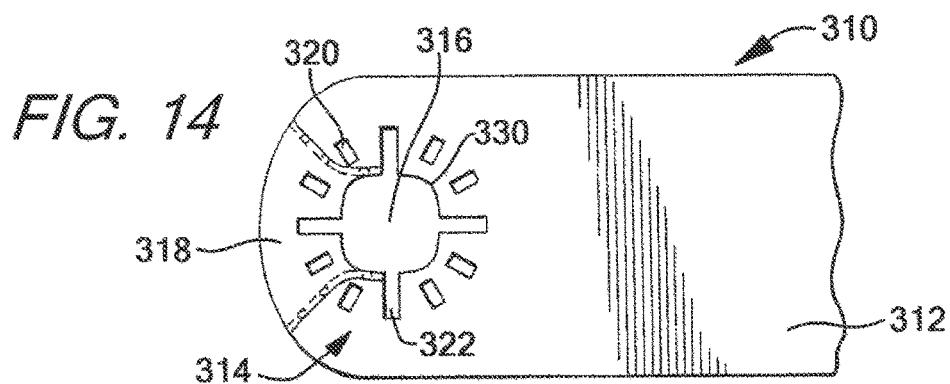
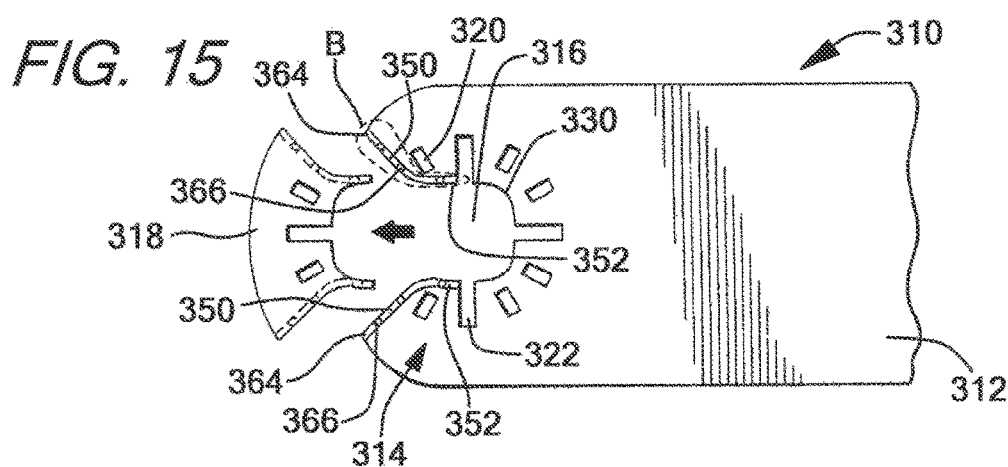
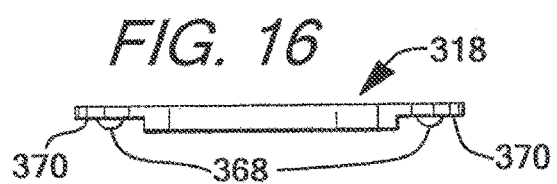
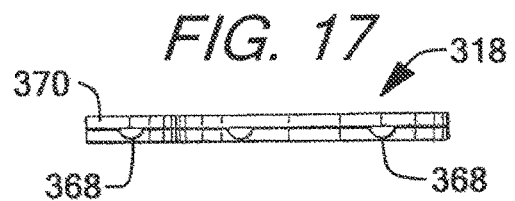
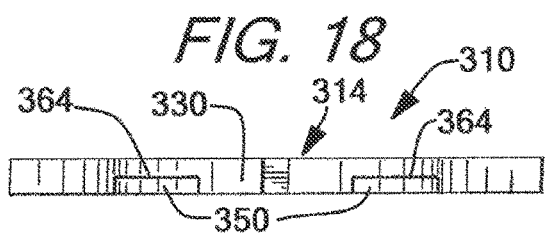

TOOL ACCESSORY HAVING A PARTIALLY REMOVABLE ATTACHMENT PORTION

RELATED APPLICATIONS

None.

FIELD OF THE INVENTION

The present invention relates to tool accessories, and more specifically to tool accessories for power tools.

BACKGROUND OF THE INVENTION

Tool accessories come in a variety of shapes and sizes in order to be utilized with a variety of tools. In order to attach to a tool which is capable of using a particular accessory, the accessory may include an attachment element. In order to attach to some tools, the attachment portion may include apertures or through holes which attach to one or more protrusions to attach the accessory. In order to securely attach the accessory to the tool, a clamp or other fastener device may be provided which holds the accessory in place once it has engaged the tool.

Generally speaking, for some types of tools, like for example oscillating tools, a main aperture is required to connect any accessory to the tool. However, different tools may have different accessory connection configurations. For example, some tools may require that a tool accessory have a completely enclosed or surrounded main aperture for connection. Some tools may require or be usable with an accessory which has a main aperture which is partially open. Additionally, some tools or attachment elements may have a series of protrusions for mating with a series of apertures, receptacles, or slots formed in the attachment portion of the accessory.

For tools which can utilize both a fully enclosed or partially open main aperture, having a partially open main aperture is advantageous insofar as it allows for the accessory to be disengaged, or re-engaged with the tool without having to completely remove any clamp or other fastener used to hold the tool accessory in place. With a partially open main aperture, the clamp or other fastener device can be partially loosened so as to disengage the tool accessory, and allow the tool accessory to loosen up and disengage the tool without having to fully remove the clamp or fastener. The clamp or fastener may be loosened up, and the tool accessory may be slid off of the tool and disengaged through the open main aperture. This is generally faster than having to fully remove the clamp or fastener, and reduces the possibility of the clamp or fastener being lost when changing tool accessories.

It would be advantageous if a single tool accessory were capable of being utilized with multiple tools, regardless of the connection configuration of the tool.

It would be further advantageous if the single tool accessory were capable of being modified as need for use with multiple tools.

It would be further advantageous if the single tool accessory were capable of having a selectively enclosed or partially open main aperture for engaging the tool.

The present invention is directed to solving these and other problems.

SUMMARY OF THE INVENTION

The present invention is directed to a tool accessory for use with tools which is capable of multiple attachment configurations, and capable of attaching to multiple tools.

According to one aspect of the invention, a tool accessory having an attachment portion having a first aperture for attaching to a tool, and a removable portion. In a first configuration, the removable portion is engaged with the attachment portion, and in a second configuration the removable portion is disengaged from the attachment portion.

The tool accessory may be an accessory intended for use with an oscillating tool. The tool accessory may further include at least one additional aperture configured to receive at least one protrusion from a tool or at least one attachment element used to connect the tool accessory to a tool. Alternatively, or in addition to the at least one aperture, the at least one tool accessory may include at least one slot configured to receive at least one protrusion from a tool or at least one attachment element used to connect the tool accessory to a tool.

The removable portion of the tool accessory may have a scored or perforated connection with the attachment portion. The removable portion may be disengaged from the attachment portion by mechanical means, such as bending it with a pliers or vice grips. Although a scored or perforated section has been disclosed, it will be understood by those with ordinary skill in the art that other means for providing a structurally weakened, and, in turn, breakable portion of the tool accessory can be employed to facilitate mechanical removable of the removable portion.

In another embodiment, the tool accessory may include at least one channel formed as part of the attachment portion. The channel may be capable of receiving, guiding, and engaging the removable portion of the attachment portion. In order to facilitate engagement in the first configuration, the tool accessory may include at least one shoulder located at one end of the at least one channel proximate the first aperture. The at least one shoulder may engage the removable portion in the first configuration. In order to accommodate the shoulder, or the channel, and provide a uniform first aperture and surface for the tool accessory, the removable portion of the tool accessory may include at least one cutout or cutout portion. The at least one cutout portion may engage the shoulder in the first configuration when the removable portion is engaged with the attachment portion. The at least one cutout portion may further, or alternatively, extend longitudinally along an edge of the removable portion so as to fit within the channel formed in the attachment portion. Where no shoulder is located proximate the aperture, the tool accessory may include a fastener for holding the removable portion in place when in the first configuration. The fastener may be used to connect the removable portion to the attachment portion in the first configuration.

In yet a further embodiment, the removable portion may include at least one protrusion while the attachment portion includes at least one receptacle. The at least one protrusion formed in the removable portion may be capable of being capable of engaging or mating with the at least one receptacle in the first configuration to hold the removable portion in place while engaged. The at least one protrusion may then also being capable of disengaging the at least one receptacle to allow the removable portion to disengage the attachment portion in the second configuration.

These and other aspects and attributes of the present invention will be discussed with reference to the following drawings and accompanying specification and claims.

BRIEF DESCRIPTION OF THE DRAWINGS

FIG. 6 shows a top view of a tool accessory in the first configuration as contemplated by the invention;

FIG. 7 shows a top view of a tool accessory in the second configuration as contemplated by the invention;

FIG. 8 shows a back view of a tool accessory in the second configuration as contemplated by the invention;

FIG. 9 shows a side view of a removable portion of a tool assembly in the second configuration as contemplated by the invention;

FIG. 10 shows a top view of a tool accessory in the first configuration as contemplated by the invention;

FIG. 11 shows a top view of a tool accessory in the second configuration as contemplated by the invention;

FIG. 12 shows a back view of a tool accessory in the second configuration as contemplated by the invention;

FIG. 13 shows a close up of portion A in FIG. 11;

FIG. 14 shows a top view of a tool accessory in the first configuration as contemplated by the invention;

FIG. 15 shows a top view of a tool accessory in the second configuration as contemplated by the invention;

FIG. 16 shows a back view of a removable portion of a tool accessory in the second configuration as contemplated by the invention;

FIG. 17 shows a side view of a removable portion of a tool assembly in the second configuration as contemplated by the invention;

FIG. 18 shows a back view of tool accessory in the second configuration; and

FIG. 19 shows a view of portion B from FIG. 15.

DETAILED DESCRIPTION OF THE PRESENT INVENTION

Figure 1:
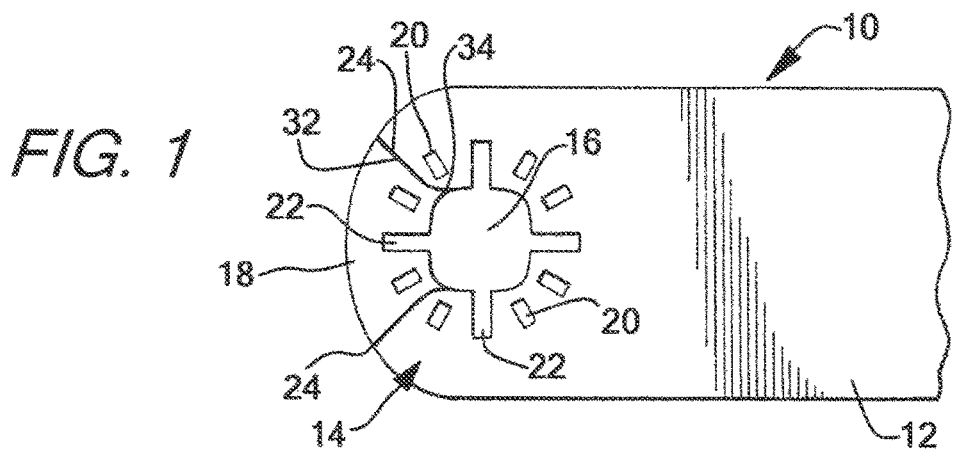
FIG. 1 shows a top view of a tool accessory in the first configuration as contemplated by the invention.

While the present invention is susceptible of embodiment in many different forms, there is shown in the drawings and will herein be described in detail several preferred embodiments of the invention with the understanding that the present disclosure is to be considered as an exemplification of the principles of the invention and is not intended to limit the broad aspect of the invention to the embodiments illustrated.

FIG. 1 shows a top view of an embodiment of a tool accessory as contemplated by the present invention. Tool accessory 10 including a working portion or end 12 and an attachment portion or end 14. The attachment portion includes a first or main aperture 16 and a removable portion 18. The first or main aperture may be utilized to attach the tool accessory to a tool, which may be, for example, an oscillating tool. The first or main aperture, may, for example, engage or be received on a spindle or shaft on an oscillating tool in order for the tool accessory to be used.

The tool accessory may further include at least one additional aperture 20 and at least one slot 22. Though shown throughout the application as including both additional apertures and slots, tool accessory 10 may include only additional apertures, only slots, both additional apertures and slots, or neither apertures nor slots. Including both apertures and slots, however, may allow the tool accessory to attach to multiple tools which have different engagement or attachment configurations. Any additional apertures or slots may be engaged by one or more of the tool and any attachment element associated with the tool which fixes the tool accessory in place once the tool accessory is engaged with the tool. An attachment element may be, for example, a clamp, a fastener, a disc, or some other element capable of being fixed to the tool in a manner which engages both the tool and tool accessory and fixes the tool accessory in place for use by the tool.

Figure 2:
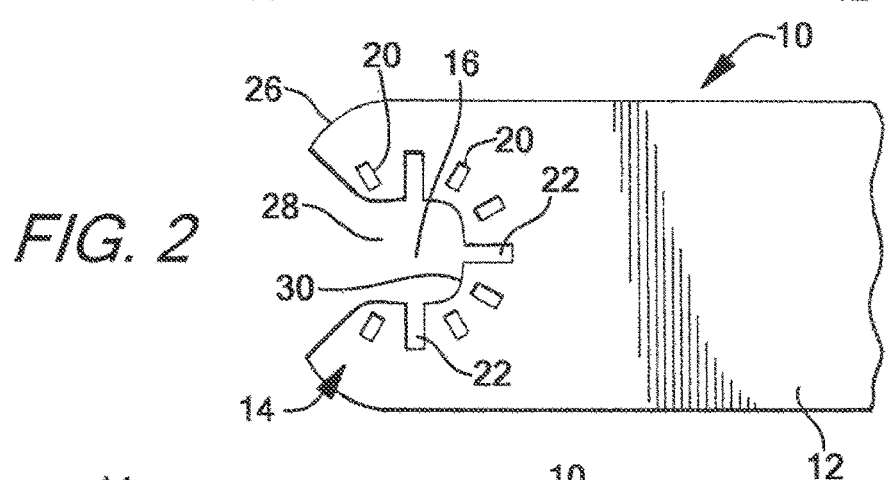
FIG. 2 shows a top view of a tool accessory in the second configuration as contemplated by the invention.

FIG. 1 shows tool accessory 10 in a first configuration where removable portion 18 is engaged with attachment portion or end 14 of the tool accessory. Removable portion 18 may be engaged with attachment portion or end 14 utilizing a scored or perforated (or any other connection that enables mechanical removal, by, for example, a pliers or other bending method) connection 24 which may allow for the removable portion to be lifted/bent and removed or disengaged from the attachment portion. Once the removable portion is removed, tool accessory 10 will be in a second configuration whereby first or main aperture 16 is partially open along the back of the tool accessory to allow for a different connection or engagement configuration for the tool accessory. FIG. 2 shows a top view of tool accessory 10 in the second configuration.

Figure 3:
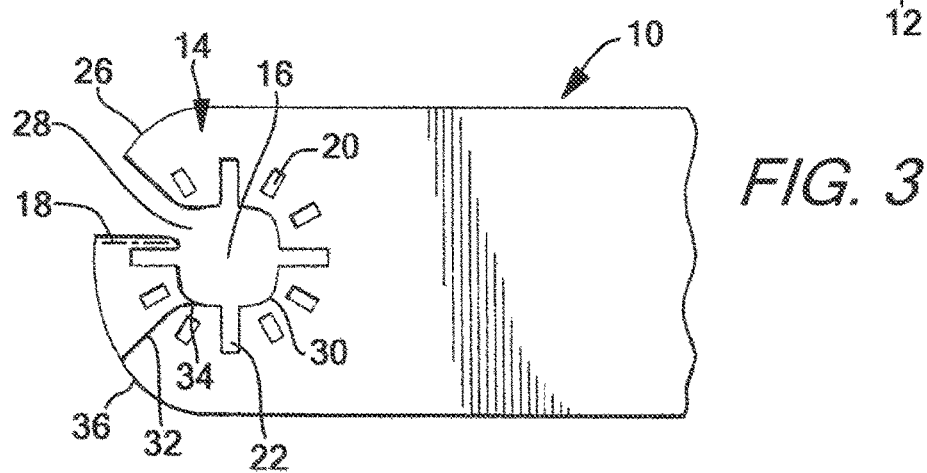
FIG. 3 shows a top view of a tool accessory transforming from the first configuration to the second configuration as contemplated by the invention.
Figure 4:
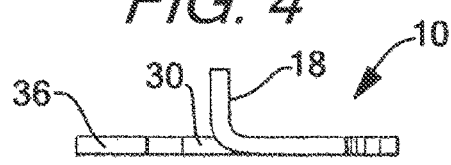
FIG. 4 shows a back view of a tool accessory transforming from the first configuration to the second configuration as contemplated by the invention.
Figure 5:
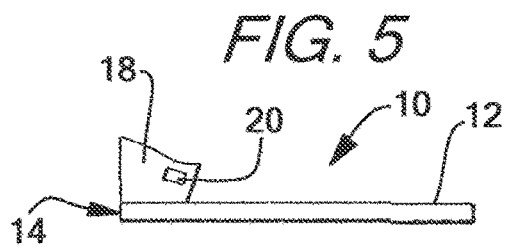
FIG. 5 shows a side view of a tool accessory transforming from the first configuration to the second configuration as contemplated by the invention.

FIGS. 3-5 show various views of a partially removed removable portion 18 in the tool accessory embodiment shown in FIGS. 1 and 2. FIG. 3, which is a top view, shows removable portion 18 being bent upwards, after one side of removable portion 18 has been disengaged form attachment portion or end 14. FIG. 4, which is a back view of tool accessory 10, and FIG. 5, which is a side view of tool accessory 10, further show the disengagement of a portion of removable portion 18 from attachment portion 14. As seen in FIGS. 3-5, after appropriate bending, removable portion 18 will completely breakaway from the too accessory so that first or main aperture 16 is opened along back edge 26 of the tool accessory to eventually provide channel 28—which can also be seen in FIG. 2. Interior portion 30 of first or main aperture 16 will remain intact for engaging a tool, as needed.

Scored or perforated connection 24 may take any form, so long as a large enough channel is created to allow tool accessory 10 to engage and disengage from a tool through channel 28. It may, as seen in FIGS. 1-5 include an angled portion 32 and a straight portion 34, however the entire connection 24 may be angled, straight, curvilinear, or any other shape which will allow for the removal of the removable portion. In order to realize the full effect of channel 28 and the opened first or main aperture, when the first or main aperture is round, for example, the channel should provide an opening at least wide enough for the connection element of a tool to fit through the channel and engage the first or main aperture.

Removable portion 18 may be removed or disengaged from attachment portion 14 using any means which will effectively breakaway the removable portion along scored or perforated connection 24. For example, pliers or vice grips may be utilized to grip the removable portion and twist or break it away from the attachment portion to disengage it. Alternatively, the removable portion may be punched or knocked out using a hammer or similar element.

By providing removable portion 18 and any additional apertures 20 or slots 22, tool accessory 10 can be configured to connect to multiple tools having different connection configurations. The tool accessory may also be capable of realizing the advantage of having an open first or main aperture to engage and disengage the tool without having to fully remove any clamps, fasteners, or other connection elements. For tools which require a fully enclosed first or main aperture, tool accessory 10 can be left in the first configuration as shown in FIG. 1. Where a tool requires a partially open first or main aperture, tool accessory can be altered to the second configuration as shown in FIG. 2. Where the tool accessory is to be used with a tool which can use either an opened or enclosed first or main aperture, the removable portion may be left in for potential future use with a tool which requires a fully enclosed first or main aperture, or the removable portion may be disengaged from the attachment portion to allow for the easier connect/disconnect of the tool accessory from the tool.

While the embodiment of the tool accessory shown in FIGS. 1-5 are capable of use with multiple tools having different configurations, once the tool accessory is in the second configuration, putting the tool accessory back into the first configuration is generally not possible or requires great effort. In other embodiments, however, the tool accessory may be selectively put in both the first and second configuration as needed.

FIG. 6 shows a second embodiment for a tool accessory in the first configuration. As seen in FIG. 6, tool accessory 110, may include working end 112, attachment portion or end 114, first or main aperture 116, removable portion 118, and additional apertures 120 or slots 122, and a fixed interior portion 130 of the first or main aperture like the embodiment shown in FIGS. 1-5. However rather than being disengageable using scored or perforated connection, a combination of a channel, shoulder, and protrusion may be utilized to allow removable portion 118 to be engaged and in the first configuration and disengaged in the second configuration so as to open channel 128 as needed. Such a configuration will allow for the re-engagement of the removable portion after it has been disengaged so that the tool accessory is capable of repeated use with a broader number of tools.

As seen in FIGS. 7 and 9, which show the tool accessory in the second configuration and a side view of removable portion 118, removable portion 118 may include protrusions 136 which extend along the outside of the portion of the removable edge which engages the attachment portion or end of the tool accessory. Protrusions 136 may effectively extend from back edge 138 of removable portion 118, along the outside of angled portion 140, and along a portion of straight portion 142, before ending at cutout 144. Exterior portion 146 of first or main aperture 116 will form the surface of the removable portion opposite back edge 138.

In the first configuration, protrusions 136 may be received in, guided and engaged by channels 148 which are formed in attachment portion 114 of tool accessory 110. The channels can be more easily seen in FIG. 8 which is a back view of the attachment portion in the second configuration. As seen in FIG. 10, channels 148 may extend along angular portion 150, into straight portion 152 (blocked from view in FIG. 8), ending at shoulder 154. When removable portion 118 is slid fully into engagement with attachment portion 114 in the first configuration, cutout 144 and shoulder 154 may prevent removable portion 118 from over sliding/extending into first or main aperture 116. The cutout and shoulder engagement will insure a uniform first or main aperture as exterior portion 146 will align with interior portion 130 to form aperture 116 in the first configuration.

Using the protrusion and channel configuration will allow removable portion 118 to be disengaged and then re-engaged with attachment portion 114 as necessary to accommodate different tool attachment configurations, or allow tool accessory 110 to take advantage of channel 128 to more easily engage and disengage from a tool capable of using either an enclosed or partially open first or main aperture.

Though an angled and straight portion of both the channel and removable portion is discussed with respect to the embodiment shown in FIGS. 6-9, it should be understood that once again, like the embodiments shown in FIGS. 1-5, the engagement portions or connection lines may take any form which will allow the removable portion to slidingly disengage and reengage from and/or into the attachment portion.

While shown in the various embodiments throughout this application as a uniform surface, it should be understood that any tool accessory discussed herein may include any number of contours, bends, or configurations required or desired for the accessory. For example, the attachment portion or end may be formed on a first plane or at a first level, with the working end being connected by a ramped or slopped surface and formed on a second plane or second level above or below the attachment portion. Additionally, the working end may be made of or have a different thickness than the attachment end. For example, in embodiments utilizing channels and protrusions to engage and disengage the removable portion from the attachment portion, the attachment portion may have a greater thickness to accommodate the channels and protrusions engagement than is desired at the working portion.

It is also contemplated by the invention that embodiments which use channels and protrusions may not have any shoulder or cutouts to prevent the removable portion from over engaging the attachment end and extend into the first or main aperture. In order to prevent such, the shape of the angled and straight portion, or any other shape which may be used, may be altered so as to prevent over insertion or engagement of the removable portion.

In some embodiments, however, like those shown in FIGS. 10-13, a connector or fastener may be used to hold the removable portion in engagement with the attachment portion.

FIG. 10 shows an embodiment of tool accessory 210 in the first configuration. As with the embodiments shown in FIGS. 1-5 and 6-9, tool accessory 210, may include working end 212, attachment portion or end 214, first or main aperture 216, removable portion 218, and additional apertures 220 or slots 222, and a fixed interior portion 230 of the first or main aperture. In addition to those elements, in the first configuration, fasteners 256 may be utilized to hold removable portion 218 in place and keep it engaged with attachment element 214. In order to present a flush face, attachment element 214 may include receptacles 258 or the like which can receive any fastener head when the fastener is engaged with the attachment and removable portions.

In order to accommodate and receive the fastener portions, channels 248 may include transverse receiving channels 260 which will allow fasteners 256 to pass through channel 248. The transverse receiving channels can be seen in FIG. 12 which is a back view of the attachment element in the second configuration. The fasteners may pass through the receiving channels and engage a corresponding fastener aperture 262 formed in protrusion 236 of the removable portion which can be seen in FIG. 13—which is a close-up of portion A in FIG. 11, showing an edge of the removable portion in the second configuration. Fasteners 256 can be dropped down through receiving channels 260 and into fastener apertures 262 to hold removable portion 218 in place and keep it engaged in the first configuration. The remainder of the embodiment shown in FIGS. 10-13 may be kept substantially the same as the embodiment shown in FIGS. 6-9 with regards to the channels and protrusion and the respective engagement and disengagement of both.

The fastener used may be any fastener known in the art which may be fastened and unfastened once or multiple times. For example, a pin or a screw may be used. Where a threaded element like, for example a screw, is used, the interior of the transverse receiving channels and the interior of any fastener apertures may have a mating thread configuration to allow for better engagement.

An additional embodiment of a tool accessory can be seen in FIGS. 14-19. Tool accessory 310 includes working end 312, attachment portion or end 314, first or main aperture 316, removable portion 318, and additional apertures 320 or slots 322, and a fixed interior portion 330 of the first or main aperture. Rather than have any channels and/or separate fasteners, the removable portion may include a lip having at least one protrusion, and the attachment portion may include a seat having at least one mating receptacle. The removable portion may then be placed to sit on the seat of the attachment portion when engaged in the first configuration, and the mating protrusions and receptacles may engage to prevent the removable portion from disengaging.

The shoulder formed in the attachment portion can be seen, for example, in FIGS. 15, 18, and 19. As seen in FIGS. 15 and 19, which show a top view of the tool accessory in the second configuration and a close up of portion B of FIG. 15 respectively, seat 364 may extend along the entire engagement edge of the attachment portion, like for example along angled portion 350 and straight portion 352. The shoulder may include receptacles 366 which will receive the protrusions from removable portion 318 when the removable portion is engaged in the first configuration. The receptacles may be a ridge, divot or channel formed in the surface of the seat, or alternatively may be through holes through which a longitudinal protrusion may extend and engage.

The protrusions can be seen in FIGS. 16 and 17 which are back and side views of removable portion 318 respectively. As seen in FIGS. 16 and 17, protrusions 368 extend downwards from lip 370 which will overlap and engage seat 364. The protrusions may be any shape or configuration, like for example nubs or pins.

It is to be understood that additional embodiments of the present invention described herein may be contemplated by one of ordinary skill in the art and the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

What is claimed is:

1. A tool accessory comprising:
    a body comprising an oscillating tool blade and having an outer edge, and
        a working portion spaced apart from an attachment portion, the attachment portion having
            a first aperture for attaching to a tool, and
            a removable portion,
        wherein in a first configuration the first aperture is completely surrounded, and an outer edge portion of the removable portion forms a portion of the outer edge of the body, and
    in a second configuration the removable portion is disengaged from the attachment portion and the portion of the outer edge of the body formed by the outer edge portion of the removable portion is removed, opening a channel from the outer edge of the body to the first aperture.

2. The tool accessory of claim 1 further comprising at least one additional aperture, the at least one additional aperture being configured to receive at least one protrusion from a tool or at least one attachment element used to connect the tool accessory to a tool.

3. The tool accessory of claim 2 further comprising at least one slot, the at least on slot being configured to receive at least one protrusion from a tool or at least one attachment element used to connect the tool accessory to a tool.

4. The tool accessory of claim 1 further comprising at least one slot, the at least on slot being configured to receive at least one protrusion from a tool or at least one attachment element used to connect the tool accessory to a tool.

5. The tool accessory of claim 1 wherein the removable portion has a scored or perforated connection with the attachment portion, the removable portion being capable of becoming disengaged from the attachment portion at the scored or perforated connection.

6. The tool accessory of claim 1 further comprising at least one channel, the at least one channel formed as part of the attachment portion and being capable of receiving, guiding, and engaging the removable portion of the attachment portion.

7. The tool accessory of claim 6 further comprising at least one shoulder, the at least one shoulder being located at one end of the at least one channel proximate the first aperture, the at least one shoulder engaging the removable portion in the first configuration when the removable portion is engaged with the attachment portion.

8. The tool accessory of claim 7 wherein the removable portion includes at least one cutout, the at least one cutout engaging the shoulder in the first configuration when the removable portion is engaged with the attachment portion.

9. The tool accessory of claim 6 further comprising a fastener, the fastener being used to connect the removable portion to the attachment portion in the first configuration.

10. The tool accessory of claim 1 wherein the removable portion includes at least one protrusion and the attachment portion includes at least one receptacle, the at least one protrusion being capable of engaging the at least one receptacle in the first configuration while being capable of disengaging the at least one receptacle in the second configuration.

11. The tool accessory of claim 1 wherein the removable portion is capable of being selectively engaged, disengaged, and re-engaged with the attachment portion.

12. The tool accessory of claim 1, wherein in the first configuration the first aperture is completely surrounded by an interior edge portion of the removable portion and an interior portion of the first aperture, and
    in the second configuration the channel extends from the outer edge of the body to the inner portion of the first aperture.

13. A tool accessory comprising:
    a saw blade;
    an attachment portion spaced apart from the saw blade, the attachment portion having
        a circular first aperture for attaching to a tool, and
        a removable portion, wherein
    in a first configuration the removable portion and the attachment portion form an integral body, the integral body having an outer edge, wherein the removable portion bounds an exterior edge of the circular first aperture so that the circular first aperture is completely surrounded and an outer edge of the removable portion forms a portion of the outer edge of the integral body, and in a second configuration at least a portion of the removable portion is disengaged from the attachment portion, and removing the portion of the outer edge of the integral body formed by the outer edge of the removable portion and the exterior edge of the circular first aperture, opens a channel from the outer edge of the integral body to the circular first aperture.

14. The tool accessory of claim 13 wherein the surface of the attachment portion is scored or perforated, wherein the removable portion may be disengaged from the attachment portion at the scored or perforated surface.

15. The tool accessory of claim 13 further comprising at least one channel, the at least one channel formed as part of the attachment portion and being capable of receiving, guiding, and engaging the removable portion of the attachment portion.

16. The tool accessory of claim 15 further comprising at least one shoulder, the at least one shoulder being located at one end of the at least one channel proximate the circular first aperture, the at least one shoulder engaging the removable portion in the first configuration when the removable portion is engaged with the attachment portion.

17. The tool accessory of claim 16 wherein the removable portion includes at least one cutout, the at least one cutout engaging the shoulder in the first configuration when the removable portion is engaged with the attachment portion.

18. The tool accessory of claim 15 further comprising a fastener, the fastener being used to connect the removable portion to the attachment portion in the first configuration.

19. The tool accessory of claim 13 wherein the removable portion includes at least one protrusion and the attachment portion includes at least one receptacle, the at least one protrusion being capable of engaging the at least one receptacle in the first configuration while being capable of disengaging the at least one receptacle in the second configuration.

20. The tool accessory of claim 13 wherein the removable portion is capable of being selectively engaged, disengaged, and re-engaged with the attachment portion.

* * * * *